(12) United States Patent
Hammerman et al.

(10) Patent No.: US 7,074,762 B2
(45) Date of Patent: Jul. 11, 2006

(54) COMPOSITION AND METHOD FOR IMPROVING FUNCTION OF EMBRYONIC KIDNEY TRANSPLANTS

(75) Inventors: Marc R. Hammerman, St. Louis, MO (US); Sharon A. Rogers, Edwardsville, IL (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/222,460

(22) Filed: Dec. 29, 1998

(65) Prior Publication Data

US 2003/0086909 A1    May 8, 2003

Related U.S. Application Data

(60) Provisional application No. 60/070,457, filed on Jan. 5, 1998.

(51) Int. Cl.
*C07K 14/475* (2006.01)
*A61K 38/18* (2006.01)

(52) U.S. Cl. .................... 514/12; 424/93.9; 424/93.21; 435/375; 530/399

(58) Field of Classification Search ................. 514/12; 424/93.1, 93.21, 93.9; 435/375
See application file for complete search history.

(56) References Cited

U.S. PATENT DOCUMENTS

| 5,106,832 A | * | 4/1992 | Froesch ........................... 514/3 |
| 5,135,915 A | | 8/1992 | Czarniecki et al. ............ 514/21 |
| 5,273,961 A | * | 12/1993 | Clark ............................. 514/8 |
| 5,728,676 A | | 3/1998 | Halloran ...................... 514/12 |
| 5,744,304 A | * | 4/1998 | Munford ........................ 435/6 |
| 5,759,830 A | | 6/1998 | Vacanti et al. ............... 435/180 |
| 5,770,417 A | | 6/1998 | Vacanti et al. ............... 435/180 |
| 5,976,524 A | * | 11/1999 | Hammerman .............. 424/93.1 |

FOREIGN PATENT DOCUMENTS

| EP | 0 853 942 | | 7/1998 |
| WO | 97/49798 | | 12/1997 |
| WO | WO97/49798 | * | 12/1997 |
| WO | 98/50061 | | 11/1998 |

OTHER PUBLICATIONS

Chiang et al., Human Placental Lactogen Inhibits Growth Without Changing Serum Lenils of IGF-I in Rats, Acta Endocrinologica, 127 (2) 147-51 (Abs.), Aug. 1992.*
File Cpalus on STN. AN No. 1992:249442. Rogers et al. "Metanephric transforming growth factor-.alpha.-is required for renal organogenesis in vitro." Am. J. Physiol. vol. 262 (4, pt. 2) pp. F533-G539. Abstract only. 1992.*
File Medline on STN AN No. 91094244. Woolfe et al. "Creation of a functional chimeric mammalian kidney." Kidney International, vol. 38, No. 5, pp. 991-997. Abstract only. Nov. 1990.*
Chemical Abstracts. Liu et al. Abstract No. 122:179195e. p. 205. vol. 122, No. 15.*
Rogers et al. Metanephric Transforming Growth Factor Alpha is Required for Renal Organogenesis in Vitro', American J. of Physiol. vol. 262, No. 4, ot, 2. pp. F533-F539. 1992.*
Liu et al. "Trophic effect of insulin-like growth factor-I on metanephric development: Relationship to proteoglycans" Eur. J. Cell. Biol. vol. 65, No. 2, pp. 378-391. 1994.*
Woolf, MD, A.S., et al., "Integration of New Embryonic Nephrons Into the Kidney", *Amer. Jour. of Kidney Diseases*, vol. XVII, 6:611-614 (Jun. 1991).
Woolf, A.S., et al., "Creation of a functioning chimeric mammalian kidney", *Kidney Intl..*, vol. 38:991-997 (1990).
Churchill, M., "Kidney Transplants in Cyclosporine-Treated Sprague-Dawley Rats", *Transplantation*, vol. 49, No. 1:8-13 (Jan. 1990).

(Continued)

*Primary Examiner*—Anish Gupta
(74) *Attorney, Agent, or Firm*—Richard F. Trecartin

(57) ABSTRACT

A method and composition for enhancing the development of metanephric tissue upon transplantation into an allogenic or xenogenic host are disclosed. Metanephric tissue is removed from an embryonic donor and is contacted with a composition comprising one or more growth factors for metanephric development. The composition can be administered to the metanephric tissue in vitro prior to implantation of the donor tissue in the transplant recipient, or can be administered in vivo either during or subsequent to the transplantation procedure.

15 Claims, No Drawings

OTHER PUBLICATIONS

Robert, B., "Evidence that embryonic kidney cells expressing flk-1 are intrinsic, vasculogenic angioblasts", *Amer. Physiol. Soc.*, pp. F744-753 (1996).

Abrahamson, D.R., et al., "Glomerular Development Intraocular and Intrarenal Grafts of Fetal Kidneys", *Lab. Investigation*, vol. 64, No. 5:629-639 (1991).

Barakat, T.I., et al., "The capacity of fetal and neonatal renal tissues to regenerate and differentiate in a heterotopic allogeneic subcutaneous tissue site in the rat", *J. Anat.*, 110; 3:393-407 (1971).

Cooper, D.K.C., et al., "The Pig as Potential Organ Donor for Man", *Springer-Verlag*; Xenotransplantation; pp. 481-500 (1991).

Somerville, C.A., et al., "Future directions in transplantation: Xenotransplantation", *Kidney Intl..*, vol. 44; Suppl. 42:S-122-S-121 (1993).

Armstrong et al., "Embryonic Kidney Rudiments Grown in Adult Mice Fail to Mimic the Wilms' Phenotype, but Show Strain Specific Morphogenesis," Experimental Nephrology, 1(3):168-174 (1993).

Tisinai et al., "Comparison of Growth, Neovasculatization and Enzymatic Function of Fetal Intestinal Grafts in the Omentum and Renal Capsule," J. of Pediatric Surgery, 25(8):914-916 (1990).

Koseki et al., "Integration of Embryonic Nephrogenic Cells Carrying a Reporter Gene into Functioning Nephrons," American Journal of Physiology, 261(3.1):C550-C554 (1991).

Woolf et al., "Origin of Glomerular Capillaries: Is the Verdict In?" Experimental Nephrology, 6(1):17-21 (1998).

Ferrari et al., "Basic Fibroblast Growth Factor Promotes the Survival and Development of Mesencephalic Neurons in Culture," Developmental Biology, 133:140-147 (1989).

Rogers, S.A., et al., "Insulin-like Growth Factors I and II are Produced in the Metanephros and are Required for Growth and Development In Vitro", *The Jour. of Cell Biol.*, vol. 113, No. 6:1447-1453 (Jun. 1991).

Simpson, M., "Immunosuppression in Xenotransplantation", *Xenograft 25*; pp. 273-284 (1989).

Rogers, et al., "Transplantation of Developing Metanephroi into Adult Rats," Kidney International, 54:27-37 (1998).

Hammerman, M.R., "Growth factors in renal development," *Seminars in Nephrology* 15(4):291-299 (1995).

Antes, L.M., et al., "A serum-free in vitro model of renal microvessel development," *Am. J. Physiol.*, 274 (*Renal Physiol.* 43): F1150-F1160, 1998.

* cited by examiner

COMPOSITION AND METHOD FOR IMPROVING FUNCTION OF EMBRYONIC KIDNEY TRANSPLANTS

RELATED APPLICATIONS

This application is related to U.S. application Ser. No. 60/070,457, filed Jan. 5, 1998.

This invention was made with Government support from the National Institute of Health Grant/Contract No. P50 DK45181. The U.S. Government may have certain rights to this invention.

BACKGROUND OF THE INVENTION

The metanephric kidneys originate during the fifth week of gestation in humans, during day 12 of embryonic rat development, and during day 20–28 of embryonic pig development, when outgrowths of the mesonephric ducts, so-called ureteric buds, collect about their distal ends, intermediate mesoderm (metanephric blastema) located caudal to the mesonephros. The outgrowths push radially into the surrounding mass of metanephric blastema and give rise to the collecting ducts of the kidneys. The proximal ends of the ureteric bud give rise to the ureter and renal pelvis. The metanephric blastema differentiates into all of the tubular structures of the adult nephron with the exception of the collecting system. The origin of the glomerular blood vessels, is in part, extrametanephric.

Studies of metanephric organ culture have shown that kidney development in vitro is dependent upon the expression of a number of polypeptides within the developing organ. Blocking the expression or action of any of transforming growth factor alpha (TGF-α), hepatocyte growth factor (HGF), insulin-like growth factor I (IGF I) or insulin-like growth factor II (IGF II), inhibits metanephric growth and development in vitro (Hammerman M R, *Seminars in Nephrology* (1995) 15:291–299). Vascular endothelial growth factor (VEGF), is also produced by developing kidneys. Blocking VEGF activity in vivo inhibits renal vascularization (Kitamano et al., *J. Clin. Invest.* 99: (1997) 2351–2357). Exposure of developing metanephroi to vitamin A stimulates glomerulogenesis in vitro (Vilar et al., *Kidn. Intl.* 49: (1995) 1478–1487).

Once renal development is complete in a mammal, no new nephrons form. The loss of renal functional mass that occurs following insults to the adult kidney is compensated, in the short term, by hypertrophy and hyperfunction of the remaining nephrons. However, these compensatory changes are often transient and under some circumstances maladaptive in that they may lead to further loss of renal function.

End-stage chronic renal failure afflicts more than 250,000 individuals in the United States alone, most of whom are treated using dialysis, a treatment with considerable morbidity. Another treatment is renal allotransplantation, which is limited by the number of available organs for transplantation. A possible solution to the lack of organ availability is the use of renal xenografts. The clinical renal xenografts performed to date have utilized primate donors, because the closer species are phylogenetically, the more easily xenografts are accepted. The clinical experience with the use of primates as kidney donors dates from the 1960s. However, the results of xenografting of kidneys has been unsatisfactory, and this technique has remained an experimental one for three decades.

Another possible solution to the lack of organ availability is the transplantation of developing kidneys (metanephric allografts or xenografts). The allotransplantation of developing metanephroi into adult animals has been attempted by several investigators. Woolf et al., (*Kidn. Intl.*, (1990) 38:991–997) implanted pieces of sectioned metanephroi originating from embryonic mice into the cortex of kidneys of outbred mice. Differentiation and growth of donor nephrons occurred in the host kidney. Glomeruli were vascularized, mature proximal tubules were formed and extensions of metanephric tubules into the renal medulla were observed. Glomerular filtration was demonstrable in donor nephrons. In contrast to the case in newborn mice, metanephric tissue transplanted into adult mice neither grew nor differentiated, but was extruded as a poorly differentiated mass under the renal capsule.

Abrahamson et al. (*Lab. Invest* (1991) 64:629–639) implanted metanephroi from day 17 rat embryos beneath the renal capsule of adult rat hosts. Within 9–10 days post-implantation, every graft became vascularized, new nephrons were induced to form and glomerular and tubular cytodifferentiation occurred. However, signs of rejection such as hypercellular glomeruli and lymphocytic infiltrates in peritubular spaces were obvious by 10 days post-transplantation.

Robert et al. (*Am. J. Physiol.* (1996) 271:F744–F753) grafted metanephroi from embryonic day 12 mouse embryos into kidney cortices of adult and newborn mouse hosts. They demonstrated that by 7 days post-transplantation, grafts into both newborn and adult hosts were vascularized by components originating from both donor and host.

Barakat and Harrison (*J. Anat.*, (1971) 110:393–407) transplanted sections of embryonic rat metanephroi into a subcutaneous site in the abdominal wall of closely related or unrelated adult rats. Lymphocytic infiltration of the graft and replacement of the graft by fibrosis occurred in both related and unrelated adult hosts, but was more rapid in the unrelated hosts.

Growth factors have been used for the purpose of reducing transplant rejection and improving transplant function. U.S. Pat. No. 5,135,915 to Czarniecki et al., describes immersing grafts in a formulation comprising transforming growth factor for a period of a few minutes up to several days prior to transplantation. The pretreatment with TGF-β purportedly reduces transplant rejection. U.S. Pat. No. 5,728,676, to Halloran describes the administration of insulin-like growth factor (IGF) before, during, or after organ transplantation for the purpose of inhibiting transplant rejection. In a canine renal autotransplantation model, it was found that storing the removed kidneys in a preservation solution supplemented with IGF-I for a period of 24 hours prior to transplantation back into the dog, significantly improved renal function for the first 5 days following transplantation (Petrinec et al., *Surgery* (1996) 120(2):221–226).

SUMMARY OF THE INVENTION

A method and composition for enhancing the development of metanephric tissue upon transplantation into an allogenic or xenogenic host are disclosed. Metanephric tissue is removed from an embryonic donor and is contacted with a composition comprising one or more growth factors for metanephric development. The composition can be administered to the metanephric tissue in vitro prior to implantation of the donor tissue in the transplant recipient, or can be administered in vivo either during or subsequent to the transplantation procedure.

DETAILED DESCRIPTION OF THE INVENTION

The methods described in published European application no. 0 853 942 A2 are applicable to the present invention. The entire contents of that application are incorporated herein by reference. To summarize, that application describes the transplantation of metanephric tissue from an embryonic mammalian donor to an allogenic or xenogenic mammalian recipient. The recipient can be at any developmental stage, including juvenile and adult. A preferred recipient is a human with reduced renal function. The metanephric tissue is taken from the donor at a suitable stage of development, typically within 1 to 5 days after the metanephros begins formation, and is implanted into the recipient either within the omentum, preferably adjacent a host kidney, or under the renal capsule of a host kidney. The metanephric tissue grows and becomes vascularized, in large part by the recipient to form a chimeric kidney. The chimeric kidney develops to form mature structures, including a ureter, which can externalize urine formed by the chimeric kidney after connection to the host's excretory system.

In experiments where rat metanephric allografts were transplanted into the abdominal cavity of non-inbred adult rat hosts, the metanephric tissue developed into functioning chimeric kidneys which were not rejected by the host for as long as 32 weeks after transplantation. It is believed that the vascularization of the metanephric tissue by the recipient facilitates the acceptance of the transplant. In contrast, when developed kidneys from adult rat donors are transplanted into non-inbred adult rat hosts, they are rejected within 7 days.

The present invention is directed to the further discovery that growth factor treatment of the metanephric tissue before, during, and/or after transplantation, enhances the development and functioning of the chimeric kidney. In addition, the removal of host renal tissue prior to transplantation of the donor metanephric tissue further enhances development of the chimeric kidney.

As used herein, the phrase "growth factor for metanephric development" refers to any molecule that promotes the growth, proliferation, and/or differentiation of metanephric tissue. Thus, the phrase encompasses growth factors, ligands that bind to growth factor receptors, vitamins, and other molecules that assist in the development of metanephric tissue. The phrase also encompasses molecules that stimulate endogenous production of growth factors for metanephric development either by the donor metanephric tissue or by the transplant recipient. For example, somatotropin is known to stimulate IGF-I production. Whether a particular growth factor assists in metanephric development can be readily determined by routine experimentation using the procedures described herein.

Presently preferred growth factors include transferrin, prostaglandin $E_1$ ($PGE_1$), sodium selenite, ligands of the EGF-receptor such as transforming growth factor alpha, epidermal growth factor (EGF), and amphiregulin; insulin-like growth factors (IGFs), particularly IGF-I and IGF-II vitamin A and derivatives thereof such as retinoic acid; vascular endothelial growth factor (VEGF); hepatocyte growth factor (HGF), nerve growth factor (NGF), cytokines such as TGF-β and other members of the TGF-β family (see Atrisano et al., *J. Biochemica et Biophysica Acta* (1994) 1222:71–80), and growth hormone (GH) (see Hammerman, M. R., *Seminars in Nephrology* (1995)). Using known procedures, it can readily be determined whether a particular factor serves as growth factor for the developing metanephroi. For example, in cultures of metanephroi, antibodies can be used to block the action, if any, of a certain factor. An inhibition of development compared to controls indicates whether the factor acts as a growth factor for metanephroi development. As another method, comparisons of development of metanephroi in culture with and without supplements can be used to determine whether a certain factor acts as a growth factor (see Hammerman et al., *Pediatr Nephrol* (1993) 7(5):616–620); Hammerman M R, *Seminars in Nephrology* (1995) 15:291–299; Schofield P N and Boulter C A, *Exp'l Nephrology* (1996) 4:97–104; Pugh et al. *Kidney Int* (1995) 47(3):774–781); Humes et al., *Lab Invest* (1991) 64(4):538–545); and Vilar et al. *Kidney Int*. (1996) 49(5): 1478–1487).

The metanephros can be treated with a single growth factor that enhances development, or combinations of growth factors can be administered either sequentially, or as a growth factor cocktail. Preferred growth factor cocktails comprise any combination of two or more of the following growth factors: transferrin, $PGE_1$ sodium selenite, nerve growth factor, fibroblast growth factor (FGF), platelet derived growth factor (PDGF), IGF-I, IGF-II, TGF-α, TGF-β, HGF, and/or VEGF. The growth factors are dissolved in any physiologically-acceptable solution in which the metanephroi can be immersed. Various cell culture media can be used, such as a 50:50 mixture of Dulbecco's modified Eagles medium and Hams F12 (DMEM:HF120). Physiological saline is another suitable solution, particularly if the growth factors are administered to the transplant recipient during or after the transplantation procedure. The growth factors are usually used at concentrations ranging from about 1 fg/ml to 1 mg/ml. Concentrations between about 1 to 100 ng/ml are usually sufficient for most growth factors. Simple titration experiments can be performed to readily determine the optimal concentration of a particular growth factor.

Prior to the transplantation procedure, metanephric tissue is harvested from one or more suitable mammalian donors at an appropriate stage of fetal development. Preferably, the metanephric tissue is harvested soon after the metanephric kidney begins formation and prior to the presence of blood vessels that either originate within the metanephros or from inside or outside the metanephros. If the embryonic renal tissue is harvested too early in development, it may, once implanted into the recipient, differentiate into non-renal tissues such as hair and gut. Tissue harvested too late in the development of the metanephric kidney, for example, tissue having visible blood vessels, may contain more antigen-presenting cells and cell-surface antigens and thus present more of threat of rejection by the recipient. Preferably, the harvested metanephroi contains metanephric blastema, segments of ureteric bud, and nephron precursors, and does not contain glomeruli.

The preferred developmental stage for harvesting the metanephros will vary depending upon the species of donor. Generally, the metanephros is preferably harvested 1 to 5 days after the metanephros forms. Preferably, the metanephros is harvested from 1 to 4 days after the metanephros forms, and more preferably from about 2 to 4 days after metanephros formation. In rats, the metanephros forms on day 12.5 of a 22-day gestation period, and on day 11 of a 19 day gestation period in mice. In these species, a suitable time frame in which to harvest the donor metanephros of mice or rats is typically between the second and fourth day after the metanephros begins formation. Preferably the metanephros is harvested within 3 days after formation of the metanephros begins.

In species having a longer gestation period, the timeframe during which the metanephros is preferably harvested following its formation, can be longer. Generally, the time frame in which the metanephros is harvested will be less than about one fifth of the total gestation period of the donor, preferably less than about one seventh of the total gestation period of the donor, and more preferably, less than about one tenth of the total gestation period of the donor. Table 1 shows the time-course (in days) of metanephros development and gestational period in some vertebrates.

TABLE 1

|  | Metanephros Formation (days) | Gestational Period (days) |
| --- | --- | --- |
| Human | 35–37 | 267 |
| Macaque | 38–39 | 167 |
| Pig | 20–30 | 114 |
| Guinea Pig | 23 | 67 |
| Rabbit | 14 | 32 |
| Rat | 12.5 | 22 |
| Mouse | 11 | 19 |
| Hamster | 10 | 16 |

Pigs are preferred xenogeneic donors for humans because of their comparable organ size, and availability. Additionally, the digestive, circulatory, respiratory and renal physiologies of pigs are very similar to those of humans. In the case of renal function, the maximal renal concentrating ability (1080 mOsm $l^{-1}$), total renal blood flow (3.0–4.4 ml $min^{-1}$ $g^{-1}$) and glomerular filtration rates (126–175 ml $min^{-1}$ 70 kg) of the miniature pig are virtually identical to those of humans (see Sachs D H, *Veterinary Immunology and Immunopathology* (1994) 43:185–191). The use of metanephroi from transgenic pigs that have been "humanized" to reduce the potential for transplant rejection may provide further advantages (e.g. Pierson et al., *J. Heart Lung Transplant* (1997) 16:231–239). Pig metanephroi are harvested at about the 10 mm stage. This occurs between approximately embryonic day 20 and embryonic day 30. Human tissue could be used as an allogeneic source for transplantation.

Metanephroi are removed surgically under a dissecting scope and suspended in a suitable holding medium, such as a 1:1 mixture of Dulbecco's modified Eagles Medium and Hams F12 medium (Rogers et al. *J. Cell Biol.* (1991) 113:1447–1453), and placed under sterile conditions, until they are transplanted. It is preferred to use the whole metanephros, with renal capsule intact, for transplantation. One or more metanephroi may be used per recipient, depending upon the increase in nephron mass that the recipient needs.

If the metanephroi are to be treated with growth factors prior to transplantation, the growth factors can be added directly to the holding medium. When used as a pretreatment, the growth factor composition exerts a positive effect in a surprisingly short period of time. Significant improvement in the development of the implant can be achieved when the metanephric tissue is contacted with the growth factor composition in vitro for less than 24 hours. Preferably, the metanephric tissue is contacted with the growth factor composition in vitro for less than 8 hours, and preferably less than 2 hours. Optimal results can usually be achieved when the metanephric tissue is contacted with the growth factor composition for as little as about 20 to 60 minutes prior to implantation into the transplant recipient.

To transplant the metanephric tissue, surgery is performed on the recipient to expose one or both kidneys. Surgical procedures for renal transplantation are well known in the art (e.g. Cohn et al., *Am. J. Physiol* (1982) 24:F293–F299). The donor metanephroi can be implanted directly under the renal capsule of the recipient's kidney, or into a fold of the omentum where it forms a chimeric kidney that functions independently of the recipient's kidney. The omentum is a membranous structure which connects the bowels. It is a preferred site for the implant, particularly if the implanted metanephric tissue is intended to replace a malfunctioning or non-functioning kidney which may be removed, either at the time of transplantation or after the donor metanephric tissue develops sufficiently to form a functioning chimeric kidney. Implantation of the metanephric tissue into the omentum is also preferred if it is desired to treat the tissue with growth factors after implantation. The omentum is a more accessible site for the growth factor treatment compared to underneath the renal capsule of the recipient's kidney. An osmotic pump that provides a steady supply of growth factors could be placed in the omentum next to the implanted tissue. Alternatively, the recipient could receive periodic injections of the growth factors in the vicinity of the transplant or the growth factors could be delivered in a manner such that they are present in the recipient's blood that circulates through the transplant.

While a donor metanephros can be placed adjacent to any portion of the omentum, it is preferable to implant it in an omental fold which will retain the developing kidney at the site of implantation. It is most preferable to implant the metanephros at an omental fold located near one of the recipient's kidneys, particularly near the ureter, so that the developing ureter of the metanephros can be readily connected to the recipient's excretory system.

When implanted into the recipient's kidney, an incision, large enough to receive the donor tissue is made in the fibrous renal capsule that surrounds the recipient kidney. The location of the incision can be anywhere in a viable portion of the recipient kidney, but most conveniently will be at an external border of the kidney that is easily accessible during surgery. The donor tissue is placed between the capsule and the cortex of the recipient kidney.

The implanted metanephroi are allowed to grow and differentiate within the recipient under conditions that allow the metanephric tissue to vascularize and develop to form mature, functioning nephrons. Suitable conditions may include the use of pre or post-operative procedures to prevent rejection of the implant in addition to the use of growth factors that facilitate the development and functioning of the metanephric tissue. In some cases of allogeneic transplantation, there may be no host rejection of the transplanted metanephros. However, in the case of xenogeneic transplantation, rejection prevention measures are typically taken. This is usually done by immunosuppressing the recipient after the transplantation. Cyclosporine A (CSA) treatments can provide sufficient immunosuppression to prevent rejection of the donor tissue. CSA treatment protocols to prevent transplant rejection are known in the medical field. Local immunosuppression techniques are described by Gruber, *Transplantation* (1992)54:1–11. In U.S. Pat. No. 5,560,911, antibodies directed against idiotypes on naturally occurring human anti-animal antibodies are disclosed for use in inhibiting xenograft rejection. The anti-idiotypic antibodies are injected into the xenograft recipient in order to bind to the idiotypes expressed on anti-xenograft antibodies. Anti-idiotypic antibodies that bind human anti-pig antibodies, to prevent rejection of transplanted pig tissues by a human patient are exemplified. Anti-lymphocyte globulins are also known for prevention of transplant rejection (Lacy et al. *Diabetes*, (1981) 30:285–291). As an alternative to immunosuppression, the implanted metanephros can be treated prior to transplantation to reduce its antigenicity. Exemplary approaches to the reduction of immunogenicity of transplants by surface modification are disclosed by Faustman WO 92/04033 (1992). For xenografts into human transplant recipients, transgenic animals that have been humanized to reduce organ transplant rejection may be used. Finally, agents thought to induce tolerance to transplanted tissue can be administered to recipients such as CTLA4-lg (Lin et al., *J. Exp. Med.* (1993) 178:1801–1806).

Metanephric kidneys transplanted using the techniques described herein grow, and become vascularized in large part by the recipient, to form chimeric kidneys. It is believed that the vascularization by the recipient may facilitate the acceptance of transplanted xenogeneic tissue. When implanted into the recipient's kidney, the metanephroi become imbedded into the parenchyma of the recipient kidney. The donor metanephroi begin to form various mature structures that are distinguishable from the structures in the adjacent recipient renal tissue, including mature glomeruli and tubules, renal papilla, and ureter. After a sufficient period of development, it is evident that the glomeruli are capable of filtering plasma. Hence, implantation of the metanephric tissue contributes to an increase in the nephron mass of the recipient.

Filtering glomeruli are evidenced by the detection of urine within the donor metanephroi. This can be done by measuring the levels of urea nitrogen and/or creatinine in fluid aspirated from the donor tissue. Such fluid may be contained within one or more cysts associated with the donor tissue (see Example 1). Urine is defined herein as fluid having a concentration of creatinine and/or urea nitrogen that is higher than the concentration of the corresponding components found in the recipient's plasma. The concentration differential varies, and will be reduced with increased hydration of the recipient. However, generally, the concentration of creatinine in the donor metanephroi will be at least twice the concentration found in the recipient's plasma. The concentration of urea nitrogen in the donor metanephroi will generally be at least fifty percent greater than the concentration of urea nitrogen in the recipient's plasma.

In order to facilitate the externalization of the urine that forms within chimeric kidney, a standard ureter to ureter anastomosis procedure can be used to hook up the ureter that forms from the implanted metanephros with the ureter of a kidney of the recipient. During this procedure, the chimeric kidney can be further treated with growth factors by direct administration of a growth factor-containing composition to the chimeric kidney as it is exposed during the procedure. When the metanephroi are implanted into the omentum of the recipient, externalization of urine can be achieved by linking the ureter directly to the recipient's ureter or bladder. These procedures, and other procedures known in the art for the externalization of urine are summarized in *Adult and Pediatric Urology*, 3rd Ed., Gillenwater, et al., Eds. ¶. 987–994 and 2369–2375 (1996). In some cases, post-transplantation surgery may be unnecessary as the intrarenal transplanted donor kidneys may incorporate into the collecting system of the host.

All cited references are incorporated herein by reference.

In order that the invention described herein may be more fully understood, the following examples and are set forth. It should be understood that these examples are for illustrative purposes only and are not to be construed as limiting the scope of the invention in any manner.

EXAMPLE 1

Allogeneic Transplantation of Metanephroi into Host Kidney

Transplantation Methods:

Whole metanephroi, with renal capsules intact, were removed surgically under a dissecting scope from E15 Sprague-Dawley rat embryos (Harlan, Indianapolis Ind.), and suspended in saline solution on ice under sterile conditions. Within 45 minutes after removal, four metanephroi per recipient were implanted under the capsule of normal kidneys of 6 week old outbred normal (NL) female Sprague-Dawley rats. Some of the recipient rats had undergone contralateral nephrectomy (UNX) or unilateral nephrectomy and one-half contralateral kidney infarction ( 1½ NX) using previously described procedures (Rogers et al., supra). Transplanted metanephroi were approximately 700 μm in diameter and, as would be expected for this stage of development, contained segments of ureteric bud and some developing nephron precursors, but no glomeruli. When noted, recipient rats received Cyclosporine A (CSA) beginning post-transplantation (5 mg/kg body weight per day injected subcutaneously) in vehicle (peanut oil). As a control, vehicle only was injected.

Structural Development of Metanephroi:

Four or six weeks later, kidneys were removed from the rats. When recipient kidneys were examined post-transplantation, cysts containing clear fluid surrounded the sites where metanephroi were transplanted under the capsule of NL, UNX or 1½ NX rats. Structures resembling small kidneys approximately 7 mm (7000 μm) in diameter were present under the cysts and were embedded into the larger recipient kidney. Thus, the diameter of the transplanted metanephroi had increased 10-fold reflecting a 1000-fold increase in volume. Histological examination of fixed, paraffin-embedded, and sliced sections of the tissue mass stained with hematoxylin and eosin revealed that the structures were integrated into the parenchyma of recipient kidneys, and that clusters of lymphocytes were present at the transplant-recipient interface.

Metanephroi transplanted into kidneys of vehicle-treated rats that had undergone UNX underwent growth, development and vascularization in vivo. They contained mature glomeruli and tubules that could be distinguished from glomeruli and tubules in adjacent recipient renal tissue by their smaller size and different staining characteristics in paraffin sections stained with hematoxylin and eosin. Blood vessels were present in transplanted metanephroi. Some were identifiable as arteries. Glomeruli in transplanted metanephroi contained red blood cells, distinguishing them from glomeruli of rat metanephroi grown in organ culture, in which vascularization does not occur. Cysts were present within the parenchyma of transplanted metanephroi that contained structures resembling a renal papilla. Other structures were lined with transitional epithelium characteristic of the ureter. Lymphocytes accumulated around the periphery of transplanted metanephroi, but there was no evidence of rejection of tubular or vascular elements. Similar growth, development and vascularization of metanephroi transplanted into rats that had undergone UNX or into kidneys of NL rats were observed.

Metanephroi transplanted into kidneys of CSA-treated 1½ NX rats were examined 4 weeks post-transplantation.

Results of such transplantations were similar to those into kidneys of vehicle-treated 1½ NX rats except no peripheral lymphocytes were observed.

Integration of Transplanted Metanephroi into Recipient Renal Tissue:

To determine whether transplanted metanephroi became integrated into recipient kidneys, kidneys of NL rats 6 week post-transplantation were examined. To clear blood from the organ, kidneys were perfused using a modified Ringers solution injected into the aorta distal to the renal arteries following occlusion of the aorta proximal to the kidneys and transection of the inferior vena cava. This results a blanching of the kidney as blood is replaced by perfusate. Normally, the entire kidney blanches as described by Bortz et al., (J. Cell Biol., (1988) 107:811). However, following perfusion of kidneys that contained a transplanted metanephros, blood remained in the transplanted structure relative to the recipient kidney. Most likely, this reflects a reduced perfusion in chimeric blood vessels (derived from transplant and host kidneys) that have been shown to supply transplanted metanephroi relative to perfusion in those supplying the host kidney (Robert et al., Am. J. Physiol., (1996) 271:F744). Blood could be traced into the papilla of the recipient kidney.

Kidneys were stained using tetragonobolus purpurea lectin (TPL), as described by Rogers et al., Am. J. Physiol. (1993) 264:F996, which is expressed in collecting ducts of developing rat kidneys prior to birth and for several weeks following birth, but not in collecting ducts of kidney from adult rats. In adult rat kidney, TPL is expressed in distal tubules and medullary thick ascending limbs of Henle's loop. In recipient kidney tissue, TPL was expressed in cortex within distal tubule and medullary thick ascending limb as would be expected. However, TPL was also expressed in a population of collecting ducts which radiate from the transplanted metanephros into the papilla of the recipient kidney together with blood vessels, evidencing that the collecting system and blood supply of the transplanted metanephros become incorporated into the papilla of the recipient kidney.

Testing of Chimeric Kidney Function:

Levels of urea nitrogen and creatinine were measured in aspirated cyst fluid, and in blood from the aorta, and urine from the bladder of the 1½ NX vehicle-treated rats using previously described methods (Rogers et al., supra). Levels of urea nitrogen were increased 2.6-fold and 15-fold, respectively, in cyst fluid and bladder urine relative to blood, and levels of creatinine were increased 12-fold and 28-fold, respectively, as shown in Table 2 (All measurements were made at the time of sacrifice; comparisons were made using the multiple comparison procedure described by C. W. Dunnett, J. Am. Statistical Assoc. (1955) 50:1096). Thus, both urea nitrogen and creatinine were concentrated in cyst fluid relative to blood, indicating that the cyst fluid was urine. The concentrations of urea nitrogen and creatinine in the cyst fluid were significantly less than the concentrations in bladder urine, indicating that the cyst urine did not originate from leaked bladder urine. This is consistent with reports that the ability of a 4 week-old kidney (transplanted kidney) to clear the blood of urea nitrogen and creatinine relative to a 10 week-old kidney (recipient kidney), is reduced [Aperia et al., Am. J. Physiol., (1975) 228:1319].

TABLE 2

| Plasma Creatinine/ureaN* | Cyst Fluid Creatinine/ureaN* 1½ NX rats (n = 7) | Bladder Urine Creatinine/ureaN* |
|---|---|---|
| 1.14 ± .08/53.8 ± 6.3 | 13.4 ± 2.2/136 ± 16 | 32.3 ± 5/800 ± 72 |

Creatinine
Plasma < cyst fluid, $p < 0.01$
Cyst fluid < bladder urine, $p < 0.01$
UreaN (urea nitrogen)
Plasma < cyst fluid, $p < 0.01$
Cyst fluid < bladder urine, $p < 0.01$
*mg/dl

EXAMPLE 2

Xenogeneic Transplantation of Metanephroi into Host Kidney

Metanephroi from N.I.H. Swiss mouse metanephroi (E14) were transplanted underneath the renal capsule of 1½ NX Sprague Dawley rats. Following implantation, host rats were treated with cyclosporine A (CSA) (5 mg/kg body weight injected subcutaneously once per day), or vehicle (peanut oil). Four weeks post-transplantation, all that remained of the metanephroi implanted into the kidneys of rats that did not receive CSA treatment was a mass of fibrotic tissue. However, in CSA-treated recipients metanephroi grew, vascularized and developed. The presence of a urothelial-lined cavity containing a renal papilla in the transplanted metanephroi indicated that glomerular filtration occurs in the donor renal tissue.

EXAMPLE 3

Allogeneic Transplantation of Metanephroi into Host Omentum

Metanephroi were dissected from E15 sprague-Dawley rats as previously described in Example 1 and implanted into 6 week old outbred UNX Sprague Dawley rats and into rats that had no native renal tissue removed, in omental folds near the recipients' kidneys. Recipient rats received no immunosuppression post-transplantation.

After 6 weeks, transplanted metanephroi were removed and examined. They had assumed a kidney-like shape in situ, had intact ureters and were approximately one-third the diameter of native kidneys. Sections of transplanted metanephroi were prepared and stained with hematoxylin and eosin. Both cortical and medullary tissue were present. Cortices contained well-developed glomeruli containing red blood cells, proximal tubules with well-developed brush border membranes, and distal tubules. Medullas contained well-developed collecting ducts. Ureters were lined with transitional epithelium. Rare accumulations of lymphocytes were observed, but there was no evidence of rejection of tubular or vascular elements.

In contrast to finding in rats that underwent unilateral nephrectomy at the time of implantation, little or no growth of metanephroi occurred when they were implanted in rats that had no native tissue removed.

EXAMPLE 4

Connection of Implanted Metanephros to Bladder and Demonstration of Inulin Clearance in Transplanted Metanephroi Metanephroi were dissected from E15 sprague-Dawley rat embryos as previously described in Examples 1 and 3 and implanted within 45 minutes in the omentum of anaesthetized 6 week old female UNX Sprague Dawley (host) rats. During the same surgery, the host rats had undergone unilateral nephrectomy using methods described by Miller et al., *Am. J. Physiol* (1990) 259:747–751.

Six weeks following transplantation, end-to-end ureter-oureterostomy was performed using microvascular technique (interrupted 10-0 suture) between the ureter of an implanted metanephros and the ureter of the kidney that had been removed. Four weeks later all remaining native renal tissue (the contralateral kidney) was removed from host rats, following which inulin and creatinine clearances were measured on conscious rats after placement of an indwelling bladder catheter and intravenous line as described by Miller et al. *Proc. Natl. Acad. Sci.* (1992) 89:11876–11880. Baseline measurements for inulin were performed on urine and blood samples obtained prior to beginning the inulin infusions. These "background" values were subtracted from measurements performed after beginning the inulin infusion. Infusion of inulin was begun only following removal of all remaining native renal tissue and drainage of all urine remaining in the bladder (10–20 µl). Only the implanted metanephros remained connected to the bladder. As a control, an attempt was made to measure clearances in rats that had undergone bilateral nephrectomy, but had no transplanted metanephros connected to the bladder. However, in contrast to the case in rats with a transplanted metanephros connected to the bladder (results discussed below), no urine appeared in the bladder catheter over a 3 hour collection time in rats that had no transplanted metanephros.

Plasma creatinines at the time of measurements (following removal of all native renal tissue) were $1.3 \pm 0.06$ mg/dl, approximately 0-times normal. Inulin and creatinine clearances were $0.11 \pm 0.02$ and $0.65 \pm 0.18$ µl/min/100 g body weight respectively (mean±SE). The mean body weight of rats was $238 \pm 3.0$ g. The mean weight of metanephroi was $71 \pm 15$ mg. The mean volume of urine collected during 3 hours was $49 \pm 13$ µl. Inulin and creatinine clearances in a group of 5 normal rats of similar size were $0.92 \pm 0.14$ and $0.84 \pm 0.12$ ml/min/100 g respectively.

To define the relationship between the length of time post implantation and inulin clearance by metanephroi, clearances were measured at 12–16, 20–24 and 32 weeks post-implantation. The data, which is summarized in Table 3, demonstrate that metanephros cleared inulin from the host's circulation for the full length of the experiment, as long as 32 weeks after implantation. The magnitude of clearances did not change significantly as a function of time. The weights and appearance of the transplanted metanephroi also did not change as a function of time in hosts.

TABLE 3

| Time after implantation (weeks) | Inulin clearance (µl/min/100 g rat weight) | Weight (mg) |
|---|---|---|
| 12–16 (n = 7) | 0.23 ± 0.6 | 72 ± 3.8 |
| 20–24 (n = 5) | 0.31 ± 0.13 | 88 ± 9.7 |
| 32 (n = 3) | 0.34 ± 0.6 | 76 ± 23 |

Data are expressed as mean ± SEM.

EXAMPLE 5

Further Reduction of Host Renal Mass at the Time of Implantation or IGF-I Administration to Host to Enhance Metanephros Development The weights of transplanted metanephroi into the omentum of rats that had undergone unilateral nephrectomy with partial contralateral renal infarction at the time of implantation were increased more than 2-fold (145 vs 71 mg) and inulin clearances expressed per gram of kidney weight were increased more than 12-fold compared to values obtained in rats that underwent unilateral nephrectomy without partial contralateral renal infarction. Urine volumes ($145 \pm 24$ µl/3 hours) were also significantly increased ($p<0.005$, Student's t test). These observations, coupled with the finding that growth and development of transplanted metanephroi do not occur if no native renal mass is removed at the time of implantation, indicate that the stimulus that results in compensatory renal growth following reduction of renal mass (see Miller et al., *Am. J. Physiol.* (1990) 259:747–741) may also enhance the growth and development of transplanted metanephroi.

In further experiments, metanephroi were surgically dissected from E15 Sprague-Dawley rat embryos and implanted within 45 minutes in the omentum of anaesthetized 6 week old female Sprague Dawley (host) rats. During the same surgery, host rats underwent unilateral nephrectomy, using the same procedures as described in Example 4. Four weeks following transplantation, end-to-end ureter-oureterostomy was performed using microvascular technique between the ureter of a metanephros implanted in the omentum and the ureter of the kidney that had been removed. Three days following ureteroureterostomy, recombinant human IGF I (Genentech Inc., South San Francisco, Calif.) was administered by Alzet pump infusion (60 µg/day/animal) into some of the rats. Eight to 12 weeks later, all remaining native renal tissue (the contralateral kidney) was removed from host rats. For rats receiving IGF I treatment, growth factor treatment was ceased two days prior to removal of the contralateral kidney. An indwelling bladder catheter and intravenous line (see Rogers et al. *Kidney Inter'l* (1998) 54:27–37) were placed into the rats. Inulin clearances were then measured on conscious rats. Baseline measurements for inulin were performed on urine and blood samples obtained prior to beginning the inulin infusions. These "background" values were subtracted from measurements performed after beginning the inulin infusion. Infusion of inulin was begun only following removal of all remaining native renal tissue and drainage of all urine remaining in the bladder (10–20 µl). Only the implanted metanephros remained connected to the bladder.

Inulin clearances at 12–16 weeks post-transplantation were measured in metanephroi from IGF I treated rats and rats that received no IGF I. As shown in Table 4 below, administration of the IGF significantly increased inulin clearances. Weights of metanephroi were not significantly higher in IGF I treated rats. The appearances of of the transplanted metanephroi were similar in IGF I-treated and non-treated animals.

TABLE 4

|  | Implant (N = 70) | Implant/ IGF I Treatment |
|---|---|---|
| Weight (mg) | 72 ± 10 | 87 ± 11 |
| Urine volume (µl/hr) | 31 ± 9 | 47 ± 10 |
| Inulin Clearance (µl/min/100 g) | 0.23 ± 0.06 | 0.62 ± 0.13* |

TABLE 4-continued

|  | Implant (N = 70) | Implant/ IGF I Treatment |
|---|---|---|
| (µl/min/g KW) | 8.67 ± 2.83 | 19.8 ± 4.12* |
| (µl/min/rat) | 0.60 ± 0.18 | 1.70 ± 0.41* |

*Implant/IGF I treatment > Implant, p < 0.05 Student's test
Data are expressed as mean ± SEM

EXAMPLE 6

Growth Factor Treatment at the Time of Ureteroureterostomy to Enhance Development of Chimeric Kidney Four weeks following transplantation of metanephroi into the omentum of UNX rats, end-to-end ureterostomy was performed between the ureter of the transplanted metanephros and the ureter of the kidney that had been removed from the host. For 45 minutes after ureteroureterostomy, some metanephroi were bathed in 25 µl of a 50:50 mixture of Dulbecco's modified Eagles medium: Hams F12 (DMEM: HF12) containing recombinant human VEGF (Genentech Inc. South San Francisco Calif.) or DMEM:HF12 containing no additions.

Eight to twelve weeks later all remaining native renal tissue was removed from host rats, following which inulin clearances were measured in hosts. Inulin clearances of transplanted metanephroi that had been bathed with VEGF at the time of ureteroureterostomy (n=3) (1.6±0.37 µl/min/100 g) were elevated significantly (p<0.05, Student's t test) compared to clearances in metanephroi that were not treated with VEGF (n=4) (0.21±0.06 µl/min/100 g). Urine volumes of metanephroi that had been bathed with VEGF (184±26 µl/hour) were elevated significantly compared to urine volumes of non-treated metanephroi (34±10 µl/hour).

EXAMPLE 7

Growth Factor Pretreatment to Enhance Development of Chimeric Kidney

For 45 minutes prior to implantation into 1½ NX host rats, metanephroi taken from day 15 embryonic rats were incubated at 4° C. in 25 microliters of a 50:50 mixture of Dulbecco's modified Eagles medium:Hams F12 (DMEM: HF12) with or without growth factors. The growth-factor containing solution contained $10^{-7}$ M IGF-I, $10^{-7}$ M IGF-II, $10^{-8}$ M TGF-$\alpha$, $10^{-9}$ M HGF and 25 µg VEGF. The metanephroi were implanted into the recipient rats using the methods described in Example 4. Ureteroureterostomies were performed 4 weeks later. Twelve weeks after ureteroureterostomies were performed, inulin clearances were measured in host rats after removal of all remaining native renal tissue. Following measurement of inulin clearance, metanephroi were removed from the hosts and weighed.

As shown in Table 5, weights of metanephroi that had been incubated in DMEM:HF12 containing growth factors were not different from weights of metanephroi that were incubated in DMEM:HF12 without growth factors. However, inulin clearances and urine volumes were increased 3–4 fold in metanephroi that had been incubated with the growth factors compared to values in metanephroi that had been incubated without growth factors.

TABLE 5

| Group | Inulin clearance (µl/min/100 g rat weight) | Weight (µg) | Urine volume (µl/hour) |
|---|---|---|---|
| UNX+ (n-5) | 0.43 ± 0.16*** | 84 ± 24 | 34 ± 7.1 |
| UNX+ and growth factors | 1.35 ± 0.11 | 71 ± 8.9 | 145 ± 8.6** |

*UNX+ and growth factors > UNX+, p < 0.001, Multiple comparison procedure (C. W. Dunnett, supra).
Data are expressed as mean ± SEM.

EXAMPLE 8

Transplantation of Pig Metanephroi

The techniques for harvesting metanephroi, transplanting metanephroi into a recipient and for reducing host renal mass are similar to those employed on mice and rats, as described in Examples 1–6, except that microsurgical techniques are not necessary. Rather, surgeries are performed in an operating room using standard surgical techniques appropriate to large animals (see Cohn et al., supra).

Metanephroi are surgically dissected under a dissecting microscope from pig embryos at an appropriate stage of embryonic development, which is approximately gestation week 4–6. If developed metanephric vasculature is evident and/or a significant number antigen-presenting cells are present, then less developed metanephroi are obtained. If the metanephroi do not sufficiently differentiate upon implantation, then metanephroi are obtained at a later developmental stage. Within 45 minutes of removal from the donor animals, the metanephroi are implanted the omentum of anaesthetized adult (host) pigs. During the same surgery, one kidney is removed (UNX) from the host pig, or a unilateral nephrectomy and partial contralateral renal infarction (1½ NX) is performed.

In light of the fact that allogeneic transplantation of metanephroi into adult rats using the above-described methods does not result in transplant rejection, it is expected that rejection of the pig metanephroi by the host pig will not occur. However, if rejection does occur, immunosuppression protocols can be devised using routine procedures.

After the implanted metanephroi have developed to the extent that ureters have formed, end-to-end ureteroureterostomy is performed using surgical technique (interrupted suture) between the ureter of a metanephros implanted in the omentum and the ureter of the kidney that had been removed. At the same time, or up to about 6 weeks later depending upon the size and developmental state of the transplanted metanephros, all remaining native renal tissue (i.e. the remaining contralateral kidney) is removed from the host so that only the implanted metanephros remains connected to the bladder.

Baseline measurements for inulin are performed on urine and blood samples obtained prior to beginning the inulin infusions. These "background" values are subtracted from measurements performed after beginning the inulin infusion. At various time points following the removal of the contralateral kidney, inulin and creatine clearances are measured after placement of intraarterial, intravenous, and suprapubic bladder catheters into the pigs as in previous rat studies (Rogers et al., supra). The chimeric kidney that results from the procedure is considered functional if inulin clearance is greater than or equal to 10% of normal. Additional parameters are considered to evaluate the growth and development of metanephroi including the diameter of transplanted metanephroi and the presence or absence of mature glomeruli and tubules.

Techniques and methods developed in the pig allotransplantation procedures are applied in clinical trials for xenotransplantation of pig metanephroi into humans with end-stage chronic renal failure. In addition, immunosuppression methods are used.

EXAMPLE 9

Growth Factor Treatment for Increasing Inulin Clearance of Transplanted Pig Metanephroi Using methods described in Example 8, pig metanephroi are implanted into adult pigs. Growth factors are administered to the host or to the metanephroi prior to implantation and/or post implantation to increase the glomerular filtration rate of the implanted metanephroi.

In one growth factor treatment protocol, porcine somatotropin (GH) (Monsanto Chemicals, St. Louis, Mo.), which stimulates IGF I production in pigs, is administered to the host 2 mg/day IM beginning at the time of transplantation or after ureteroureterostomy. In another, IGF-I is administered to the pigs.

As another growth factor treatment, immediately after dissecting metanephroi from embryonic pigs, the metanephroi are incubated in vitro for up to 24 hours in DMEM:HF12 containing $10^{-7}$ M IGF-I, $10^{-7}$ M IGF-II, $10^{-8}$ M TGF-α, $10^{-9}$ M HGF and 1 mg/ml VEGF.

In further protocols, the in vitro and/or in vivo growth factor treatement utilizes one or more of the following growth factors: insulin-like growth factor I, insulin-like growth factor II, transforming growth factor alpha, transforming growth factor beta, acidic fibroblast growth factor, basic fibroblast growth factor, vascular endothelial growth factor, platelet-derived growth factor, nerve growth factor, transferrin, prostaglandin $E_1$, sodium selenite, vitamin A, and growth hormone.

The use of growth factor treatment in combination with reduction of native renal tissue, as described in Example 1 can be used to further enhance the function of the implanted metanephroi.

What is claimed is:

1. A method for the treatment of metanephric tissue for transplanted into a recipient comprising:
   a. contacting said metanephric tissue, in vitro, with a growth factor-containing composition comprising vascular endothelial growth factor; and
   b. transplanting said metanephric tissue into said recipient.

2. The method of claim 1 wherein said metanephric tissue is contacted with said growth factor-containing composition for less than 8 hours.

3. The method of claim 1 wherein said metanephric tissue is contacted with said growth factor-containing composition for less than 2 hours.

4. A method for the treatment of metanephric tissue transplanted into a recipient comprising contacting said transplanted metanephric tissue with a growth factor-containing composition comprising vascular endothelial growth factor, wherein said growth factor-containing composition is administered to said transplanted metanephric tissue at the time a ureteroureterostomy is performed.

5. A method for the treatment of metanephric tissue comprising contacting said metanephric tissue, in vivo, with a growth factor-containing composition comprising vascular endothelial growth factor at the time of or after being said metanephric tissue is transplanted into said recipient.

6. The method of claim 5 wherein said growth factor-containing composition is administered to said metanephric tissue by an osmotic pump.

7. The method of claim 5 wherein said growth factor-containing composition is administered to said recipient in a manner such that said vascular endothelial growth factor is present in said recipient's blood that circulates through said metanephric tissue.

8. A method for the treatment of metanephric tissue for transplantation into a recipient comprising:
   a. contacting said metanephric tissue, in vitro, with a growth factor-containing composition comprising vitamin A; and
   b. transplanting said metanephric tissue into said recipient.

9. The method of claim 8 wherein said metanephric tissue is contacted with said growth factor-containing composition for less than 8 hours.

10. The method of claim 8 wherein said metanephric tissue is contacted with said growth factor-containing composition for less than 2 hours.

11. A method for the treatment of metanephric tissue transplanted into a recipient comprising contacting said transplanted metanephric tissue with a growth factor-containing composition comprising vitamin A, wherein said growth factor-containing composition is administered to said transplanted metanephric tissue at the time a ureteroureterostomy is performed.

12. A method for the treatment of metanephric tissue comprising contacting said metanephric tissue, in vivo, with a growth factor-containing composition comprising vitamin A at the time of or after said metanephric tissue is transplanted into said recipient.

13. The method of claim 12 wherein said growth factor-containing composition is administered to said metanephric tissue by an osmotic pump.

14. The method of claim 12 wherein said growth factor-containing composition is administered to said recipient in a manner such that said vitamin A is present in said recipient's blood that circulates through said metanephric tissue.

15. The method of claim 1, 4, 5, 8, 11, or 12 wherein said contacted metanephric tissue develops into a functional chimeric kidney in said recipient and wherein the glomeruli of said functional chimeric kidney are vascularized primarily by said recipient and are able to filter plasma.

* * * * *

UNITED STATES PATENT AND TRADEMARK OFFICE
CERTIFICATE OF CORRECTION

PATENT NO. : 7,074,762 B2  Page 1 of 1
APPLICATION NO. : 09/222460
DATED : July 11, 2006
INVENTOR(S) : Hammerman et al.

It is certified that error appears in the above-identified patent and that said Letters Patent is hereby corrected as shown below:

Claim 5, Co. 16, line 9, after "after" delete -- being --.

Signed and Sealed this

First Day of April, 2008

JON W. DUDAS
*Director of the United States Patent and Trademark Office*